United States Patent
Hamilton-Vance

(10) Patent No.: US 7,341,580 B2
(45) Date of Patent: Mar. 11, 2008

(54) PROTECTIVE LINER AND A METHOD FOR USING A PROTECTIVE LINER

(76) Inventor: Colette Hamilton-Vance, 8594 Ward, Detroit, MI (US) 48228

( * ) Notice: Subject to any disclaimer, the term of this patent is extended or adjusted under 35 U.S.C. 154(b) by 0 days.

(21) Appl. No.: 11/263,621

(22) Filed: Oct. 31, 2005

(65) Prior Publication Data

US 2007/0100311 A1    May 3, 2007

(51) Int. Cl.
*A61F 13/15* (2006.01)
(52) U.S. Cl. ............... 604/385.14; 604/385.01; 604/385.11; 604/385.03; 604/385.13
(58) Field of Classification Search .......... 604/385.14, 604/385.01, 385.11, 385.03, 385.13
See application file for complete search history.

(56) References Cited

U.S. PATENT DOCUMENTS

| 4,641,381 | A |   | 2/1987  | Heran et al. |
|-----------|---|---|---------|--------------|
| 5,405,342 | A | * | 4/1995  | Roessler et al. ............ 604/364 |
| 5,649,914 | A |   | 7/1997  | Glaug et al. |
| 5,722,127 | A |   | 3/1998  | Coates |
| 6,160,200 | A | * | 12/2000 | Ehrnsperger et al. ........ 604/378 |
| 6,447,497 | B1 |  | 9/2002  | Olson |
| 6,575,953 | B2 |  | 6/2003  | Olson |
| 6,623,466 | B1 | * | 9/2003 | Richardson ............ 604/385.19 |
| 6,645,190 | B1 |  | 11/2003 | Olson et al. |
| 6,761,711 | B1 |  | 7/2004  | Fletcher et al. |
| 6,782,557 | B1 |  | 8/2004  | Feder |
| 6,783,519 | B2 |  | 8/2004  | Samuelsson |
| 6,793,650 | B2 |  | 9/2004  | Weber |
| 2004/0193135 | A1 | | 9/2004 | Van Gompel |

FOREIGN PATENT DOCUMENTS

WO    WO 00/44325    8/2000

* cited by examiner

*Primary Examiner*—Jacqueline F. Stephens
(74) *Attorney, Agent, or Firm*—Law Offices of John Chupa & and Associates, P.C.

(57) ABSTRACT

A protective liner 10 which is adapted to be selectively and removably placed within a garment 100 and which is effective to absorb waste materials emanating from a wearer of the underwear 100, having a pair of substantially identical elastic ribs 120 and a pair of substantially identical "grip tabs" 20, 22, and which obviates the need for a diaper or diaper-like product.

7 Claims, 2 Drawing Sheets

PROTECTIVE LINER AND A METHOD FOR USING A PROTECTIVE LINER

FIELD OF THE INVENTION

The present invention generally relates to a protective liner and, more particularly, to a liner which may be selectively and removably attached to the underwear or other undergarment of a wearer and which is effective to allow the underwear or other undergarment to remain clean while concomitantly allowing the wearer to become trained to use the bathroom facilities at a relatively young age, and to a method for using a protective liner in a new and novel manner.

BACKGROUND OF THE INVENTION

Typically, a baby or small child (e.g., a toddler) will wear a diaper or a "diaper-like" product (e.g., a product which resembles a diaper in form and function but which is disposable), and such a product is effective to absorb the waste excretions which emanate from the baby or small child. After the excretions occur, the diaper or diaper-like product must then be cleaned or discarded and replaced with a new such product.

While the foregoing diaper or diaper-like products do effectively absorb waste excretions, they are relatively expensive to make, are relatively inconvenient to use, replace, and/or clean, and are relatively costly to use. Further, it is known that it may be psychological desirable to quickly train a child to use the bathroom and to allow the child to quickly use underwear, thereby obviating the need for a diaper or diaper-type product.

Additionally, while liner products do exist which obviate the need for diapers, such liner-type products do not adequately protect the outer garment (e.g., fully absorb the excretions or fully act as a protective barrier), and are awkward to use and dispose of. As with the diaper-type product, although wearing these types of liner products may help a child to quickly learn to wear "regular" underwear, it may be psychologically undesirable for the child to experience "accidents" or similar incidents which are associated with current liner-type devices.

Further, both the liner and the diaper-type products are generally offered in a range of "sizes" (e.g., small, medium and large). The concept of "sizes" of protective liners or garments (e.g., an entity having static and unchangeable dimensions) means that each type of garment or liner is usable by a limited range of wearers, namely, the wearers who are the correct "size" for the garment. There is therefore a need for a protective liner-type garment which obviates the need for the liner to have a static "size", and which is therefore usable by a wide variety of wearers.

The present invention overcomes the previously delineated drawbacks associated with diaper and liner-type products, obviates the need for "sizes" and concomitantly allows a child to be quickly trained to use a conventional bathroom facility.

SUMMARY OF THE INVENTION

It is a first non-limiting object of the present invention to provide a protective liner which overcomes some or all of the previously delineated drawbacks associated with prior and/or current diaper and/or liner type products.

It is a second non-limiting object of the present invention to provide a protective liner which overcomes some or all of the previously delineated drawbacks associated with prior and/or current diaper and/or liner type products and which concomitantly allows a wearer to be quickly trained to use a conventional bathroom facility.

It is a third non-limiting object of the present invention to provide a protective liner which overcomes some or all of the previously delineated drawbacks associated with prior and/or current diaper and/or liner type products, which concomitantly allows a wearer to be quickly trained to use a conventional bathroom facility, and which may be selectively and removably attached to underwear.

It is a third non-limiting object of the present invention to provide a protective liner which overcomes some or all of the previously delineated drawbacks associated with prior and/or current diaper and/or liner type products, which concomitantly allows a wearer to be quickly trained to use a conventional bathroom facility, and which may be selectively and removably attached to underwear, and which obviates the need for sizes.

It is a fourth non-limiting object of the present invention to provide a method for using a protective liner which overcomes some or all of the previously delineated drawbacks associated with current and/or prior diaper and/or liner type products.

According to the first non-limiting aspect of the present invention, a protective liner is provided. Particularly, a protective liner of the type used in combination with a garment is provided which comprises a cup-shaped portion having a first generally smooth surface and a second opposed generally smooth surface, a pair of substantially identical "grip tab" portions, a plurality of adhesive portions and a pair of substantially identical elastic rib portions.

According to a second non-limiting aspect of the present invention, a protective liner is provided. Particularly, a protective liner of the type used in combination with a garment which comprises a cup-shaped portion, said cup-shaped portion having a first wide end adapted to cover the "seat" portion of said garment, and a second narrow end adapted to cover the "crotch" portion of said garment, and having a first generally smooth surface and a second opposed generally smooth surface, and wherein said cup-shaped portion has a longitudinal axis of symmetry which respectively crosses through said first wide end and said second narrow end, a pair of substantially identical "grip tab" portions, and wherein said substantially identical "grip tab" portions are respectively disposed at an edge of said liner along said axis of symmetry, and a plurality of adhesive portions, wherein a first one of said adhesive portions is disposed along said axis of symmetry, and wherein a second one of said adhesive portions is disposed away from said axis of symmetry, and wherein a third of said plurality of adhesive portions is disposed away from said axis of symmetry, equidistant across said axis of symmetry from said second of said adhesive portions, and a pair of substantially identical elastic rib portions, wherein each of said identical elastic rib portions is respectively disposed away from said axis of symmetry at the edge of said protective liner, and wherein said elastic ribs are adapted to be selectively extended to enlarge the size of said protective liner, and wherein each of said elastic rib portions is respectively supported by said second and third adhesive portions.

According to a third non-limiting aspect of the present invention, a method for using a protective liner is provided. Particularly, a method is provided comprising the steps of;
(a) providing a garment;
(b) providing a protective liner, said protective liner having a pair of substantially identical "grip tab" portions and also having a plurality of adhesive portions, each of which is respectively covered selectively and removably by a respective one of a plurality of adhesive backing portions, thereby exposing said plurality of adhesive portions;

(c) respectively removing each of said adhesive backing portions;

(d) selectively aligning said protective liner with a garment;

(e) selectively and removably coupling said exposed adhesive portions to said garment, thereby positioning said protective liner to collect waste-type materials;

(f) selectively grasping said "grip tab" portions and decoupling said protective liner from said garment; and (g) selectively bringing said "grip tab" portions together, thereby folding said protective liner.

These and other features and advantages of the present invention will become apparent upon a reading of the following detailed description of the preferred embodiment of the invention and by reference to the following drawings.

DETAILED DESCRIPTION OF THE PREFERRED EMBODIMENT OF THE INVENTION

Referring now to FIGS. 1-4 there is shown protective liner or protector 10 which is made in accordance with the teachings of the preferred embodiment of the invention.

Figure 1:
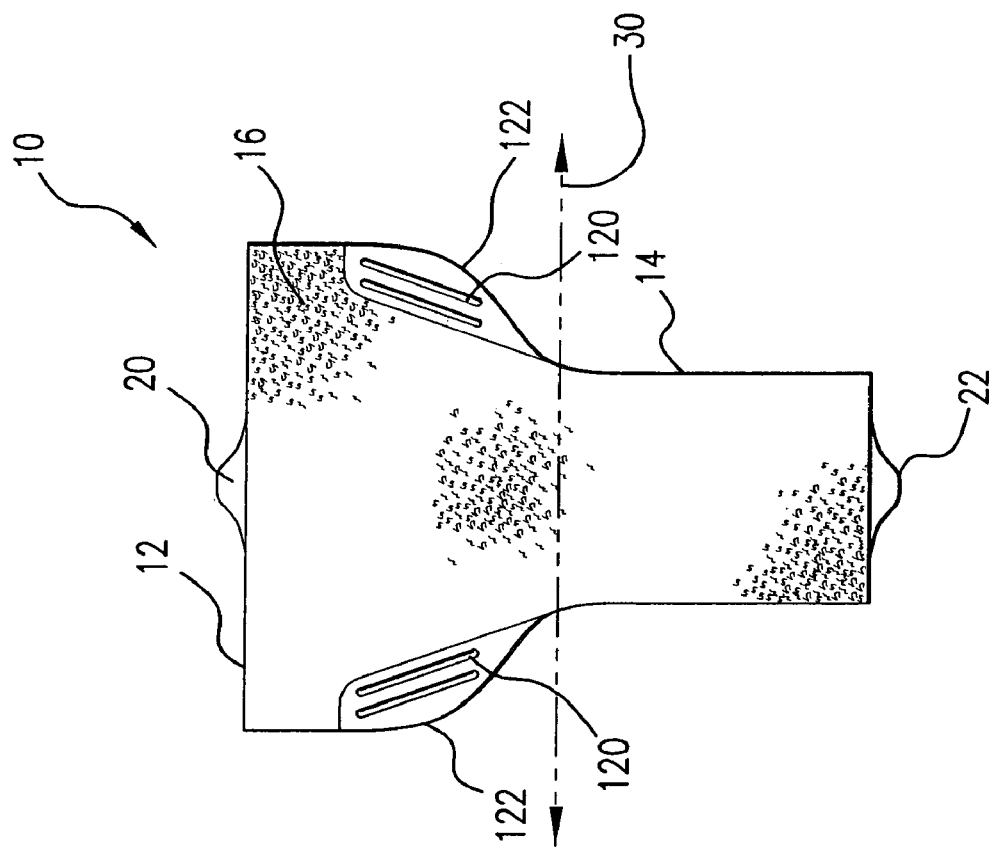
FIG. 1 is a front view of a protective liner which is made in accordance with the teachings of the preferred embodiment of the invention.

Particularly, as best shown in FIG. 1, the liner or protector 10 has a first relatively broad portion 12 which integrally terminates into a second relatively narrow portion 14. Moreover, the liner 10 includes a first relatively smooth and soft front surface 16 and a second relatively smooth and soft back surface 18. Each of the surfaces 16, 18 are substantially identical and respectively form a generally "hourglass" shape. Further, the liner 10 includes a first "grip" tab 20 which is attached (e.g., sewn into) to or which is integrally formed within and which projects from the first portion 12 and a second tab 22 which is likewise attached to or which is integrally formed within and which projects from the second portion 14. In one non-limiting embodiment of the invention, the portions 12, 14 cooperatively form a liner 10 which is substantially "cup-shaped" in cross-section. It should be appreciated that, although the most preferred embodiment of the invention includes a liner 10 which is substantially "cup-shaped" in cross-section and which has a narrow portion 14 which is substantially "longer" than the broad portion 12, the liner 10 may be of substantially any desired size and/or proportions.

Figure 2:
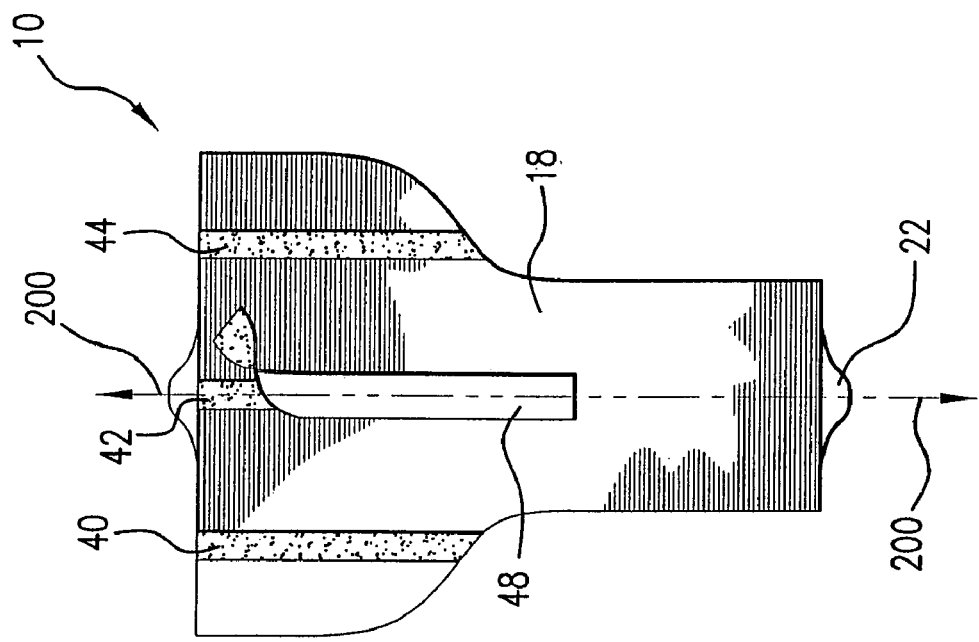
FIG. 2 is a back view of the protective liner 15 which is shown in FIG. 1.

Further, as best shown in FIG. 2, in the most preferred embodiment of the invention, the liner 10 includes a plurality of substantially identical and generally rectangular adhesive strips 40, 42, 44 which are disposed on the surface 18 (e.g., glued onto or sewn into the surface 18) and which are positioned in a manner which is substantially perpendicular to the folding axis 30. That is, in order to selectively store the liner 10, the liner 10 may be selectively folded along the axis 30 and complementary Velcro® may be applied to the portions 20, 22, thereby allowing portions 20, 22 to be selectively and removably attached or coupled together. Additionally, each of the strips 40, 42, 44 is initially and respectively covered with a selectively removable cover sheet 48. Particularly, each cover sheet 48 protects a unique one of the adhesive strips 40, 42, 44 by substantially preventing an inadvertent contact between these strips 40, 42, 44 and another object or tangible item cooperatively allowing the strips 40, 42, 44 to be selectively and individually exposed to the ambient environment in which the liner 10 resides. One of the strips, such as strip 42, may be located upon the long axis of symmetry 200 of the liner 10.

Further, in the most preferred embodiment of the present invention, the protective liner has a pair of substantially identical elastic or elastic-type ribs 120, and each of the ribs 120 is selectively and stretchably movable from a first relaxed position to a second stretched position, in which the respective ends 122 of the ribs 120 are remote from the longitudinal axis of symmetry 200 of the liner 10. In another non-limiting embodiment of the invention, the elastic ribs 120 are absent from the liner 10. Each of the ribs 120 couple surface 16 to surface 18 and may be respectively sewn or otherwise attached to the surfaces 16, 18, and each of the ribs 120 is equidistantly positioned with respect to the longitudinal axis of symmetry 200.

Figure 3:
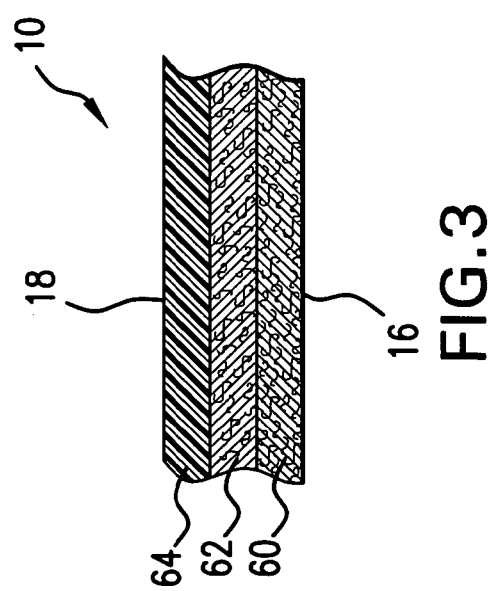
FIG. 3 is a partial side sectional view of the protective liner which is shown in FIG. 1.

Further, as shown best in FIG. 3, the protective liner 10, in the most preferred embodiments, is formed from at least three distinct or separate layers of material 60, 62, and 64. Particularly, layer 60 forms the surface 16 and comprises a relatively soft, cloth-type material which is also non-waterproof. Layer 62 comprises a material which absorbs water and other liquids and layer 64 comprises a material which is substantially waterproof and which forms surface 18. In one non-limiting embodiment of the invention, the layer 60, 62, 64 are substantially glued, attached, or otherwise affixed to one another, and thus, the liner 10 has a discernable thickness and is "cushy" and soft to touch.

Figure 4:
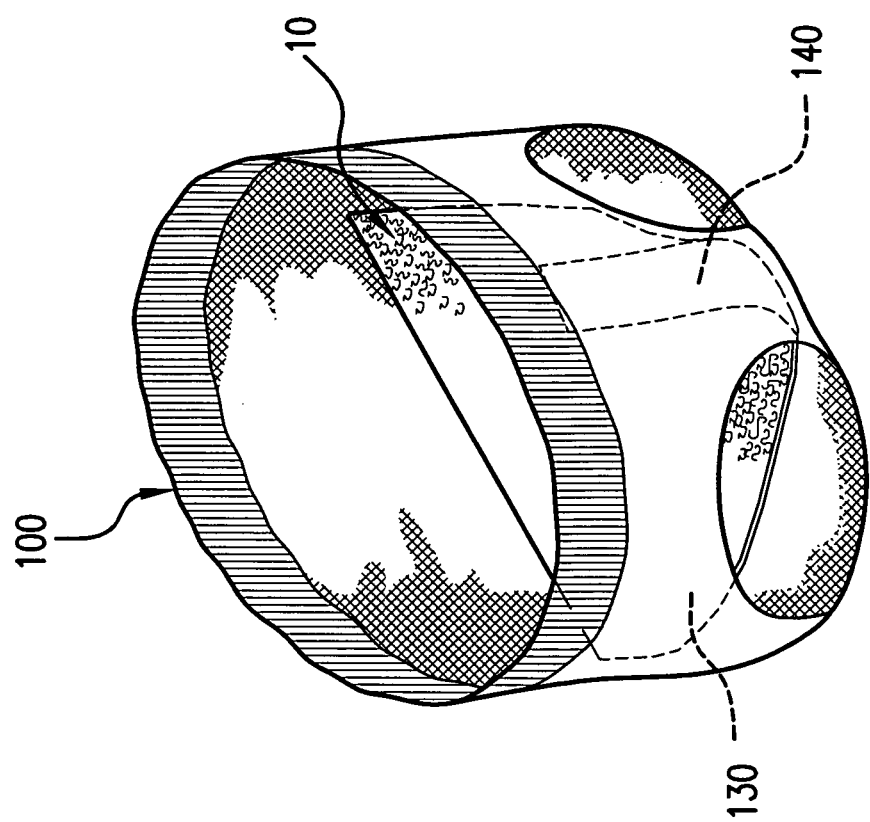
FIG. 4 is a perspective view of a pair of underwear which receives the liner which is shown in FIG. 1.

In operation, conventional underwear 100 is obtained from a store or other facility. The protective cover sheets 48 are respectively removed from the adhesive strips 40, 42, and 44 and, in the case of a male recipient, the portion 12 is coupled (by use of the exposed adhesive strips 40, 42, 44) to the inside front surface 140 of the underwear 100 and the portion 14 is coupled (by use of the exposed adhesive strips 40, 42, 44) to the seat portion 130 of the underwear 100, as shown in FIG. 4. For a female recipient, the portion 12 is selectively coupled to the seat portion 130 of the underwear 100 and the portion 14 is selectively coupled to the front inside surface 140 of the underwear 100. The difference in orientation of the liner 10 within the underwear 100 accounts for differences in the direction that waste is excreted between a male and a female (e.g., to ensure that the executed waste is substantially always directed to the liner 10 and not directly to a portion of the underwear 100.

Hence, as should be appreciated, any waste which is excreted by the wearer of the underwear 100 initially contacts and traverses the layer 60 until it reaches layer 62, where it is absorbed before it traverses to the layer of material 64. The smooth and soft surface 16 allows the liner 10 to be comfortably worn and after it becomes soiled (e.g., after waste enters barrier or layer 62), the liner 10 may be selectively removed or "pulled away" from the underwear 100. It may then be selectively folded along folding axis 30, effective to bring tabs 20, 22 into alignment with one another. If complementary Velcro® is included on the tabs 20, 22, the two tabs 20, 22 may be selectively coupled or attached to one another, effective to fold the liner in half and secure it for transport to a waste can or other garbage receptacle. Hence, the wearer may be quickly trained to use conventional bathroom facilities and "taken out of" a diaper since the liner 10 protects the underwear 100.

Further, by selective movement of the elastic ribs 120 outward (i.e., away from the axis of symmetry 200), the liner 10 may be selectively expanded to cover a larger area of the underwear. Thus, the liner 10 is selectively adaptable to a wide range of users, and obviates the need for "sizes" of protective liners, since it is sizeable to fit the specific needs of the current user.

In yet another non-limiting embodiment of the invention, an antibacterial agent or disinfectant may be applied to surfaces 16, 18 and/or an odorant may also be applied to these surfaces 16, 18.

It should be understood that the present invention is not limited to the exact construction or embodiment which is delineated above, but that various changes and modifications may be made without departing from the spirit and the scope of the inventions as are more fully delineated in the following claims.

What is claimed is:

1. A protective liner of the type used in combination with a garment, said protective liner comprising a cup-shaped portion, said cup shaped portion having a first wide end adapted to cover the "seat" portion of said garment, and a second narrow end adapted to cover the "crotch" portion of said garment, and having a first generally smooth surface and a second opposed generally smooth surface, and wherein said cup-shaped portion has a long axis of symmetry which respectively crosses through said first wide end and said second narrow end, a pair of substantially identical "grip tab" portions, and wherein said substantially identical "grip tab" portions are disposed at an edge of said liner along said axis of symmetry, and a plurality of adhesive portions, wherein a first one of said adhesive portions is disposed along said axis of symmetry, and wherein a second one of said adhesive portions is disposed away from said axis of symmetry, and wherein a third of said plurality of adhesive portions is disposed away from said axis of symmetry, equidistant across said axis of symmetry from said second of said adhesive portions, and a pair of substantially identical elastic rib portions, wherein each of said identical elastic rib portions is respectively disposed away from said axis of symmetry at the edge of said protective liner, and wherein said elastic ribs are adapted to be selectively extended to enlarge the size of said protective liner, and wherein each of said elastic rib portions is respectively supported by said second and third adhesive portions.

2. The protective liner of claim 1 wherein said first generally smooth surface is cloth, and wherein said second generally smooth surface is a non-liquid-permeable material.

3. The protective liner of claim 2 wherein an absorbent layer is disposed between said first generally smooth surface and said second generally smooth surface.

4. The protective liner of claim 3 wherein said "grip tab" portions are formed from said non-liquid-permeable second generally smooth surface.

5. The protective liner of claim 4 wherein said adhesive portions are selectively and removably covered by respective adhesive portion backing portions.

6. The protective liner of claim 5 further comprising an antibacterial agent.

7. The protective liner of claim 6 further comprising an odorant.

* * * * *